(12) United States Patent
Fischell et al.

(10) Patent No.: US 8,348,925 B2
(45) Date of Patent: Jan. 8, 2013

(54) INTRODUCER SHEATH WITH THIN-WALLED SHAFT AND IMPROVED MEANS FOR ATTACHMENT TO THE SKIN

(75) Inventors: Robert E. Fischell, Dayton, MD (US);
Tim A. Fischell, Kalamazoo, MI (US);
David R. Fischell, Fair Haven, NJ (US);
Scott J. S. Fischell, Hardy, VA (US)

(73) Assignee: Fischell Innovations, LLC, Fair Haven, NJ (US)

( * ) Notice: Subject to any disclaimer, the term of this patent is extended or adjusted under 35 U.S.C. 154(b) by 0 days.

(21) Appl. No.: 13/032,876

(22) Filed: Feb. 23, 2011

(65) Prior Publication Data

US 2012/0215174 A1 Aug. 23, 2012

(51) Int. Cl.
*A61M 25/00* (2006.01)
(52) U.S. Cl. .................................... 604/526
(58) Field of Classification Search ................ 604/526, 604/527
See application file for complete search history.

(56) References Cited

U.S. PATENT DOCUMENTS

| | | | | |
|---|---|---|---|---|
| 4,705,511 A * | 11/1987 | Kocak | ............ | 604/524 |
| 4,976,689 A * | 12/1990 | Buchbinder et al. | ........ | 604/95.04 |
| 5,069,674 A * | 12/1991 | Fearnot et al. | ................ | 604/524 |
| 5,180,376 A * | 1/1993 | Fischell | ........................ | 604/524 |
| 5,324,262 A * | 6/1994 | Fischell et al. | ............. | 604/99.04 |
| 5,360,432 A * | 11/1994 | Shturman | .................... | 606/159 |
| 5,423,774 A * | 6/1995 | Fischell et al. | ................ | 604/508 |
| 5,454,795 A * | 10/1995 | Samson | ......................... | 604/526 |
| 5,484,425 A * | 1/1996 | Fischell et al. | ................ | 604/528 |
| 5,514,236 A * | 5/1996 | Avellanet et al. | ............. | 156/154 |
| 5,630,806 A * | 5/1997 | Inagaki et al. | ................ | 604/524 |
| 5,702,373 A * | 12/1997 | Samson | ......................... | 604/527 |
| 5,704,926 A | 1/1998 | Sutton | | |
| 5,796,044 A * | 8/1998 | Cobian et al. | ................ | 174/103 |
| 5,863,366 A * | 1/1999 | Snow | ............................ | 156/143 |
| 5,879,499 A * | 3/1999 | Corvi | ........................... | 156/175 |
| 6,152,912 A | 11/2000 | Jansen et al. | | |
| 6,338,725 B1 * | 1/2002 | Hermann et al. | .......... | 604/95.04 |
| 6,533,770 B1 * | 3/2003 | Lepulu et al. | ................ | 604/524 |
| 6,939,337 B2 | 9/2005 | Parker et al. | | |
| 7,320,697 B2 * | 1/2008 | Demond et al. | ............. | 606/200 |
| 7,438,712 B2 * | 10/2008 | Chouinard | .................... | 604/527 |
| 7,815,762 B2 * | 10/2010 | Lentz et al. | ..................... | 156/84 |
| 7,905,877 B1 * | 3/2011 | Jimenez et al. | ................ | 604/525 |
| 8,034,045 B1 * | 10/2011 | Lyons | ............................ | 604/526 |
| 2001/0010247 A1 * | 8/2001 | Snow | ............................ | 156/171 |
| 2001/0044633 A1 * | 11/2001 | Klint | ............................. | 606/200 |
| 2003/0093060 A1 | 5/2003 | Kempf | | |
| 2004/0010243 A1 * | 1/2004 | Klint | ............................. | 604/526 |
| 2004/0116960 A1 * | 6/2004 | Demond et al. | ............. | 606/200 |

(Continued)

OTHER PUBLICATIONS

International Search Report and Written Opinion dated Nov. 8, 2012 for PCT/US2012/40391.

*Primary Examiner* — Kevin C Sirmons
*Assistant Examiner* — Andrew Gilbert
(74) *Attorney, Agent, or Firm* — Stoel Rives LLP (57) ABSTRACT

An introducer sheath for placement into the vascular system of a human subject. The introducer sheath has a tubular shaft, a side arm, and a hemostasis valve with an integrated attachment mechanism for attaching and detaching a proximal end of the introducer sheath to and from the skin of the human subject.

7 Claims, 7 Drawing Sheets

U.S. PATENT DOCUMENTS

| | | | |
|---|---|---|---|
| 2004/0236346 A1* | 11/2004 | Parker | 606/108 |
| 2005/0021022 A1* | 1/2005 | Sturm et al. | 606/35 |
| 2005/0060017 A1* | 3/2005 | Fischell et al. | 623/1.11 |
| 2005/0228479 A1* | 10/2005 | Pavcnik et al. | 623/1.11 |
| 2006/0064054 A1* | 3/2006 | Sakakine et al. | 604/95.04 |
| 2006/0089618 A1 | 4/2006 | McFerran et al. | |
| 2006/0095050 A1* | 5/2006 | Hartley et al. | 606/108 |
| 2006/0155302 A1 | 7/2006 | Sisken et al. | |
| 2007/0118207 A1* | 5/2007 | Amplatz et al. | 623/1.12 |
| 2008/0097516 A1* | 4/2008 | Chang et al. | 606/196 |
| 2009/0157162 A1 | 6/2009 | Chow et al. | |
| 2009/0240202 A1* | 9/2009 | Drasler et al. | 604/164.03 |
| 2010/0016837 A1* | 1/2010 | Howat | 604/527 |
| 2010/0049168 A1* | 2/2010 | Parker et al. | 604/527 |
| 2011/0160702 A1* | 6/2011 | Jimenez et al. | 604/526 |

* cited by examiner

INTRODUCER SHEATH WITH THIN-WALLED SHAFT AND IMPROVED MEANS FOR ATTACHMENT TO THE SKIN

FIELD OF USE

This invention is in the field of devices to assist in the placement of catheters through the skin to treat certain coronary and peripheral vascular disorders.

BACKGROUND OF THE INVENTION

At the present time, physicians place an introducer sheath through the skin of a patient to access that patient's vascular system. Two usual places to gain access are through the skin at the groin to enter the femoral artery and through the skin in the wrist to access the radial artery. After the introducer sheath is placed through the skin, the physician will typically use a suture to fasten the proximal end of the introducer sheath to the patient's skin. That process requires the opening of an additional package that contains the suture thread and a needle and also requires skin penetration that can be somewhat painful for the patient and has the possibility of infection.

Another problem experienced by physicians who insert vascular sheaths is the considerable force that is required to pull a guiding catheter out of an introducer sheath. Thus, any means that can reduce the frictional force experienced in pulling a guiding catheter out of the introducer sheath would be an improvement that would be appreciated by operators who perform this procedure.

Another problem with current sheaths is vascular access bleeding that sometimes occurs after the sheath has been removed. In general, there is a relationship between the outer diameter of the inserted sheath and the risk of bleeding complications. Thus, sheaths with thinner walls would decrease the size of the hole at the vascular entry site and doing that would reduce bleeding complications.

Still another problem experienced by physicians who insert vascular sheaths is the complication of accidental sheath withdrawal from the vascular entry site during the procedure, particularly when a catheter is withdrawn from the sheath. This complication can be minimized by adhesively attaching the proximal end of the sheath to the skin with an adhesive as described herein Also, making the proximal portion of the shaft of the sheath (portion in the subcutaneous tissue) less lubricious, and by decreasing the frictional force exerted on the sheath's hemostasis valve during catheter removal will decrease the propensity for the sheath to be inadvertently pulled out of the blood vessel.

SUMMARY OF THE INVENTION

A key feature of the present invention is a novel attachment means located near the proximal end of the sheath. This attachment means is designed to facilitate rapid attachment and detachment of the proximal end of the sheath to the patient's skin. One embodiment of the present invention is an introducer sheath that is improved by having an adhesive pad located at or near the sheath's proximal end that detachably attaches the introducer sheath to the patient's skin without requiring any additional parts that come from a separate sterile package such as a needle and a suture. Specifically, one embodiment of the present invention is an adhesive pad located at the distal end of the strain relief section of the shaft of the introducer sheath in close proximity to the hemostasis valve that is located at the proximal end of the introducer sheath. The adhesive pad has a pressure sensitive adhesive on one side that is covered by a removable plastic cover sheet which is removed to expose the pressure sensitive adhesive surface of the adhesive pad in order to attach the introducer sheath to the skin. Either before or after the shaft of the introducer sheath is placed through the skin, the thin plastic (or paper) cover sheet that covers the pressure sensitive adhesive is removed. When the introducer sheath is then advanced into the target blood vessel to its fully inserted position, and the plastic cover sheet of the adhesive pad has been removed, the pressure sensitive adhesive then pad is pushed firmly against the skin thereby firmly attaching the sheath to the patient's skin without requiring a sutured connection One aspect of the present invention is an adhesive pad that can be placed at a location that is in close proximity to the hemostasis valve located at the proximal end of the introducer sheath. For the first embodiment of this invention, the adhesive pad is retained at the distal end of the strain relief where it is joined to the proximal end of the shaft of the introducer sheath. If there is no strain relief, then the adhesive pad can be attached to the distal end of the hemostasis valve which is pushed against the skin when the introducer sheath is fully inserted into the patient's vascular system.

A second embodiment of the present invention uses an adhesive pad that is attached to the bottom surface of the hemostasis valve. The adhesive pad is joined to the bottom surface of the hemostasis valve through a spongy material that allows the pressure sensitive adhesive to more readily cover any skin surface even if it is somewhat irregular. A third embodiment of the present invention utilizes a pressure sensitive adhesive pad that is attached to the hemostasis valve and also wrapped around the patient's wrist. This design would be particularly applicable for the placement of the introducer sheath into the radial artery in the arm.

Another embodiment of the present invention is a diaphragm for the hemostasis valve that has a lubricity coating so as to minimize the frictional force that occurs when a catheter is either advanced or pulled back through the diaphragm of the hemostasis valve. This feature allows a catheter to be inserted into or removed from the patient's blood vessel with less resistance thus reducing the tendency to pull the introducer sheath out of that blood vessel during catheter removal. This can be combined with another novel feature using a differential of lubricity coating on the outer surface of the sheath such that a proximal portion of the sheath (portion residing in the subcutaneous tissue) would not have a lubricious (e.g., hydrophilic) coating but the more distal aspect of the outer surface of the sheath's shaft would have a lubricious coating for easy insertion through the patient's skin. This lack of lubricity coating along a proximal portion of the shaft of the sheath will tend to create some resistance to accidental sheath removal from its vascular entry site during catheter removal from the sheath.

The use of a suture is now the only means that is used to make the attachment of the proximal end of an introducer sheath to the skin. The present invention eliminates the extra time required to open a separate package containing the needle and suture material, and the time required to place the suture through the introducer sheath and into the skin. The present invention eliminates the penetration of the skin that can be somewhat uncomfortable for the patient and increases the possibility of infection. Still further, the cost of the needle and suture in a sterile pack is avoided. It is believed that suturing for retention of the sheath will require about 2 minutes of time for the operator. As a comparison, removing a plastic sheet cover from a pressure sensitive adhesive attachment to the sheath's proximal end and pushing the pressure sensitive adhesive against the skin could probably be done in only 2 seconds. Furthermore, removing the suture could again take about 2 minutes where removing the pressure sensitive adhesive pad would probably take less than 2 seconds. Such time saving and ease of use is appreciated by those physicians who perform this procedure.

Another important aspect of the present invention is the construction of the tubular shaft of the introducer sheath. Existing introducer sheaths have a wall thickness that is typically greater than 13 mils where 1.0 mil=0.001 inch. By using a flat wire helical coil with a wire thickness of approximately 1 mil to 3 mils, which coil has a very thin coating of plastic placed onto its inner and outer surfaces, it is possible to reduce the wall thickness of the tubular shaft to less than 7 mils and preferably around 5 mils. Such a novel construction would reduce the outside diameter of the introducer sheath by approximately one French size compared to existing introducer sheaths. The diameter of a catheter expressed in French when divided by three gives the diameter of the shaft in millimeters. Such a reduction in the diameter of the sheath would be highly advantageous in reducing the risk of bleeding at the groin that sometimes occurs after removal of sheaths having a larger outside diameter. Any method to decrease the requirement for surgical repair and/or a blood transfusion often needed for a major bleeding complication would be highly advantageous for the patient and would significantly decrease the morbidity, mortality and cost associated with catherization procedures. The present invention also envisions that the shaft of the sheath would employ a thin-walled, flat wire helical coil to be fabricated from a shape memory alloy such as Nitinol to prevent the possibility of kinking of the tubular shaft of the introducer sheath. Still further the present invention envisions a shaft made from two to four separate helical metal coils, one of a cobalt chromium alloy (e.g.; L605) to enhance the strength and radiopacity of the shaft and the other coil(s) to be made from stainless steel for cost economy. This novel design would be very advantageous for providing a thin-walled shaft for the sheath that is also radiopaque and reasonably economical to build. It is also envisioned that just using cobalt chromium alloy flat wires wound two at a time onto an inner Teflon layer and then coated in plastic could be an excellent design.

Still another embodiment of the present invention sheath includes an attachment component with a helical round wire having a sharpened distal end. The helical wire, which is in the form of a corkscrew, would have a handle that can be used to rotate the helical wire so that it can attach the proximal end of the sheath to the skin. This would provide an alternate means to attach and detach the sheath from the skin without the need for a separate suture.

Thus one object of the present invention is to provide a means to secure the proximal end of an introducer sheath to a patient's skin without the use of a suture, this means being integrated into the proximal region of the introducer sheath.

Another object of the present invention is to secure the proximal end of an introducer sheath to a patient's skin by means of a pressure sensitive adhesive pad without the use of a suture.

Still another object of this invention is to secure the proximal end of an introducer sheath to the skin without using a needle and suture on as to eliminate the discomfort that may be felt by the patient when a needle is used to penetrate his or her skin.

Still another object of this invention is to attach the proximal end of an introducer sheath to the patient's skin using a pressure sensitive adhesive pad attached to the hemostasis valve thereby eliminating the possibility of an infection where suture material penetrates the patient's skin.

Still another object of this invention is to place a lubricious coating on most of the outer surface of the shaft of the introducer sheath that passes through the patient's skin except for a comparatively short region that is in close proximity to the hemostasis valve at the proximal end of the introducer sheath.

Still another object of this invention is to have a shaft for the introducer sheath that has an outside diameter that is at least one French size smaller than commercially available introducer sheaths having the same inside diameter, so as to minimize bleeding complications at the vascular entry site.

Still another object of this invention is to have a shaft for the introducer sheath that uses at least two separate, thin-walled, flat wire, helical structures made from at least two different metals, this thin-walled structure having plastic materials on its inside and outside surfaces.

Still another object of this invention is to have a shaft for the introducer sheath that uses a thin-walled, flat wire, helical structure made from a shape memory alloy such as Nitinol so as to prevent kinking of the thin-walled sheath when it is inserted in the patient's vascular system, the thin-walled structure having plastic materials on its inside and outside surfaces.

Still another object of this invention is to have a method for reducing the need for a blood transfusion after an interventional procedure using an introducer sheath by reducing the outside diameter of the tubular shaft that passes through the patient's skin to access the patient's vascular system.

Still another object of this invention is to decrease the frictional force that is required as a guiding catheter is either advanced forward or pulled out of the introducer sheath by the use of a lubricity agent placed onto the diaphragm of the hemostasis valve.

Yet another object of the present invention is to have a helical wire with a handle that is attached to the proximal end of the sheath where the wire is advanced like a corkscrew to attach and detach the proximal end of the sheath to the patient's skin to reduce the time otherwise needed to get and attach a separate suture.

These and other objects and advantages of this invention will become obvious to a person of ordinary skill in this art upon reading the detailed description of this invention including the associated drawings as presented herein.

DETAILED DESCRIPTION OF THE INVENTION

Figure 1:
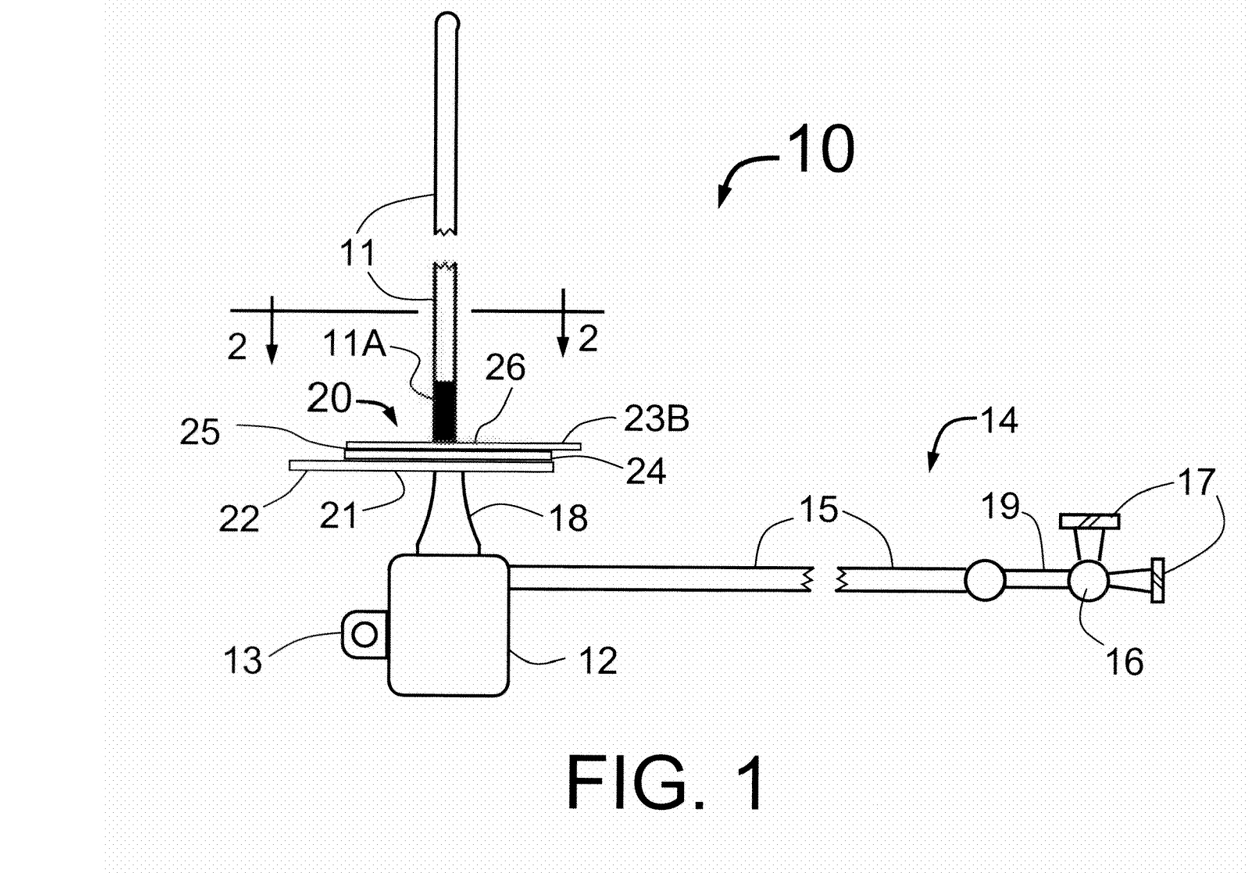
FIG. 1 is a top view of an introducer sheath having a pressure sensitive adhesive pad located at the distal end of the strain relief that is attached to the proximal end of the introducer sheath shaft.

FIG. 1 is a top view of a first embodiment of the present invention which is an introducer sheath 10 that has a tubular shaft 11 and a hemostasis valve fitting 12 located at the proximal end of the introducer sheath 10. A hydrophilic lubricious coating could be applied to the either or both the interior and exterior surfaces of the shaft 11. However, it is conceived to not extend the lubricious surface to where it passes through the patient's skin. The darkened region 11A in FIG. 1 could be the only surface of the shaft 11 that is not covered with a lubricious coating. For example, the lubricious exterior coating might extend only to within approximately 1.0 to 2 cm. from the surface of the hemostasis valve 12 and optimally the length of the region without a lubricious coating would be less than 5.0 cm. In that way, there is some increase in the tendency of the shaft 11 to be retained in the position where it is placed through the skin.

A side arm 14 of the introducer sheath 10 would have a cylindrical tube 15 which has a two-way stop cock 16 located at the proximal end of the tube 15. The valve handle 19 of the stop cock 16 can be used to select between either one of the two Luer fittings 17 or it can close off the distal end of the side arm 14. The side arm 14 is used to flush out the introducer sheath 10 before its placement into a blood vessel of a human subject and to inject medications after an interventional procedure is completed. The stop cock 16 can be closed so as to disallow any leakage of blood through the side arm 14 after the introducer sheath 10 is placed into the patient's vascular system.

Figure 2:
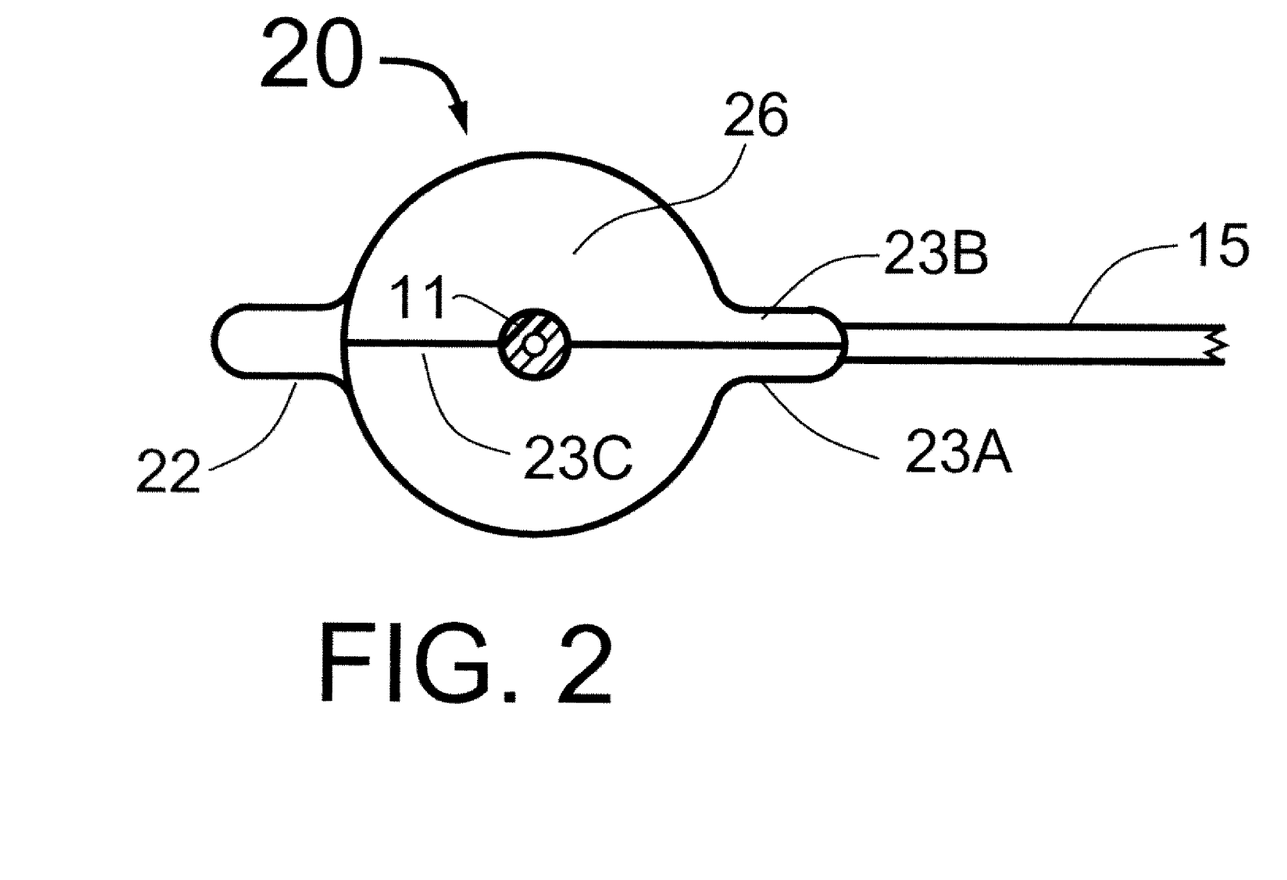
FIG. 2 is an end view of the sheath at Section 2-2 of FIG. 1.

As seen in FIGS. 1 and 2, an adhesive pad 20 is placed around the shaft 11 at the distal end of the strain relief 18. The adhesive pad 20 has a main body 24 onto which is attached a pressure sensitive adhesive 25 (as seen in FIG. 1) that is covered by a removable plastic cover sheet 26 having removal tabs 23A and 23B (as seen in FIG. 2). The plastic sheet 26 is split along the line 23C so that it can be easily removed from each side of the shaft 11. The pressure sensitive adhesive 25 is placed upon the surface of the main body 24 which main body is ideally a spongy material that is covered by a thin plastic cover sheet 21 that is fixedly attached to the spongy material of the main body 24. The tab 22 of the plastic covering 21 is used to remove the adhesive pad 20 from the patient's skin at the conclusion of the medical procedure. By the omission of an adhesive on the tab 22, it is easier for the operator to remove the adhesive pad 20 from the patient's skin at the completion of the procedure when the introducer sheath 10 is to be removed from the patient's body. Although the cover sheet 26 is shown having two pieces in FIG. 1 it could be formed as one piece or 3 or more pieces. It could also be made of regular paper, waxed paper or paper with a plastic coating. Ideally the adhesive pad 20 can be angled with respect to the longitudinal direction defined by the tube 11 so that the adhesive pad 20 can be more easily attached to the skin even if the tube 11 is inserted through the skin at an angle other than 90 degrees.

Another advantage of the design of FIGS. 1 and 2 is that the adhesive will cover the hole in the skin where the shaft 11 of the sheath 10 penetrates the skin. This covering will tend to prevent any bleeding that might otherwise occur at the place where the shaft 11 is placed through the patient's skin.

FIG. 1 also shows a suture tab 13 placed onto the side of the hemostasis valve 12. The present invention conceives of having this suture tab 13 located at the proximal end of the introducer sheath to be used if for any reason that the adhesive pad 20 fails to adequately adhere to the patient's skin. Specifically, the present invention conceives of the combination of an adhesive pad 20 with a backup of a suture tab 13.

Although FIGS. 1 and 2 show the adhesive pad 20 at a location in close proximity to the hemostasis valve 12 and wrapped around the shaft 11, it is also conceived that the adhesive pad be could be placed at other locations at or near the proximal end of the introducer sheath 10. For example, the present invention envisions an adhesive pad placed around the shaft 11 and fixedly attached to the distal surface of the hemostasis valve fitting 12 without any strain relief being used. Also, FIGS. 3, 4A, 4B, 5 and 6 illustrate alternative embodiments of the present invention each of which has an adhesive pad that is located at the proximal end of the introducer sheath with the adhesive pad attached to the hemostasis valve. It is also conceived that the adhesive layer 25 could be impregnated and elute an antibiotic medication to reduce the probability of infection at the insertion site.

Figure 3:
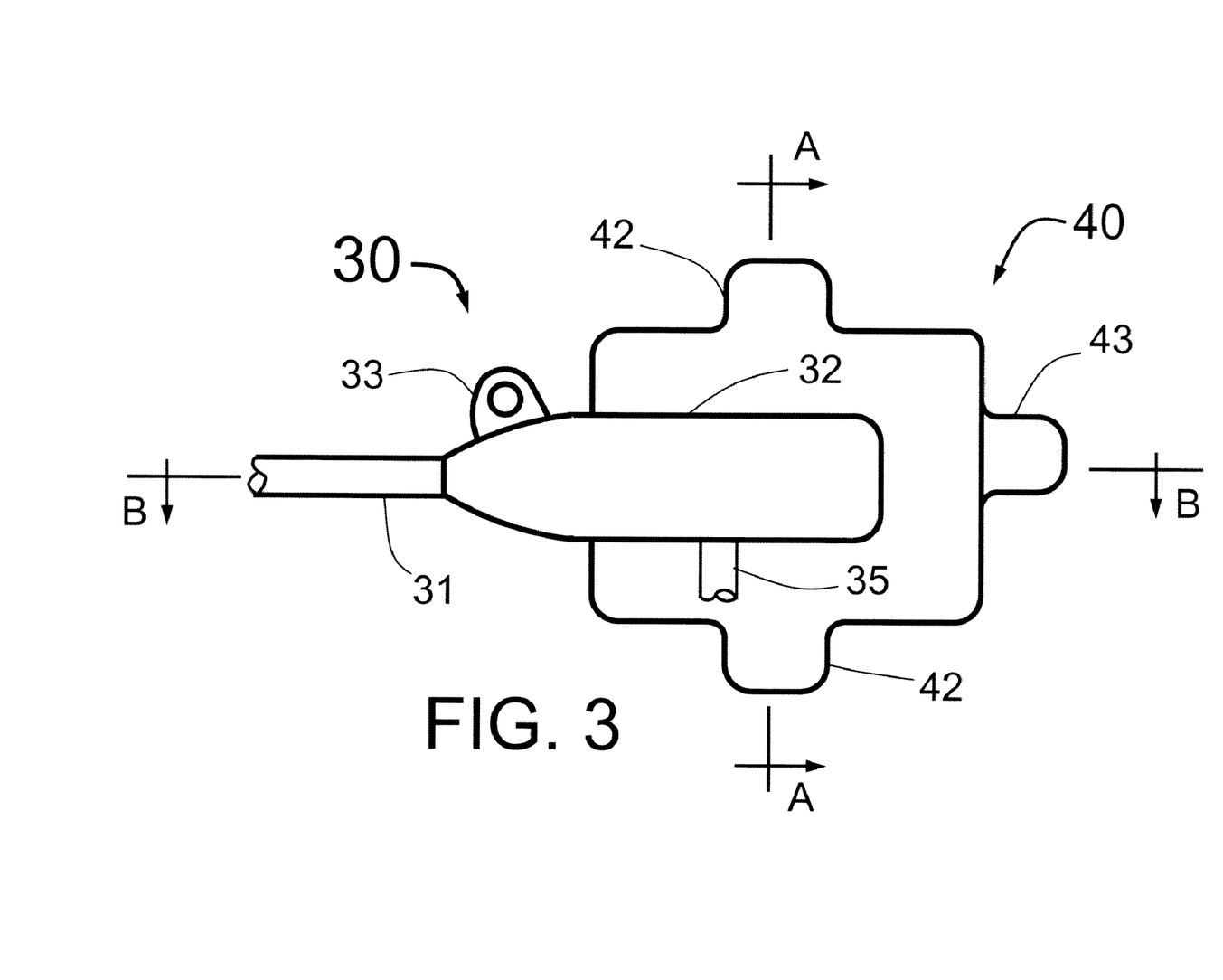
FIG. 3 is a top view of an alternative embodiment of the present invention wherein the adhesive pad is attached to the bottom surface of the hemostasis valve.
Figure 4A:
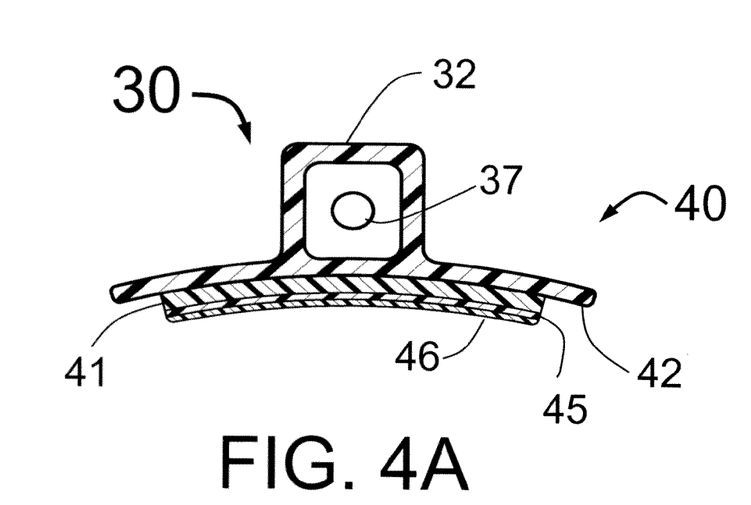
FIG. 4A is a cross section at "A-A" of FIG. 3 showing the construction of the adhesive pad and the hemostasis valve.
Figure 4B:
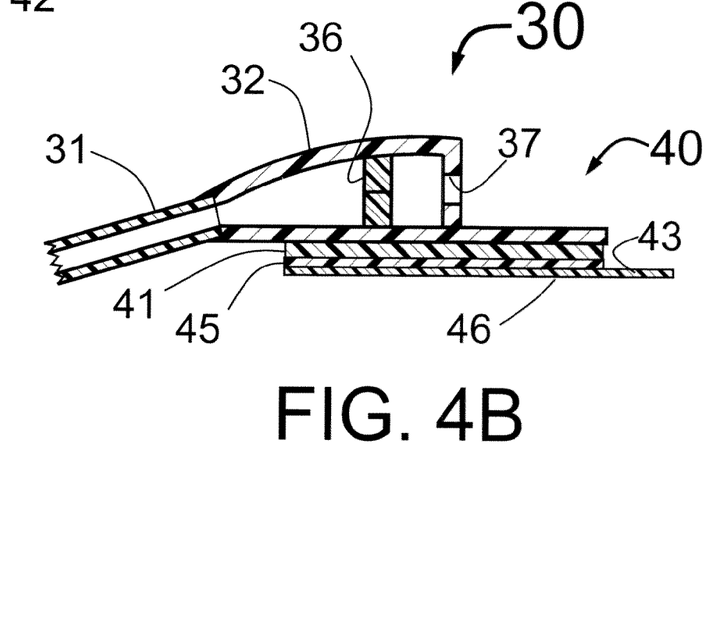
FIG. 4B is a cross section at "B-B" of FIG. 3 showing the construction of the adhesive pad and the hemostasis valve

FIG. 3 is a top view of an alternative embodiment of the present invention which is an introducer sheath 30 having an adhesive pad 40 attached to the bottom surface of the hemostasis valve 32. FIG. 3 shows a suture tab 33 that can be used with a suture as an alternative means for the operator to attach the proximal end of the introducer sheath 30 to the patient's skin. FIG. 3 also shows that the introducer sheath shaft 31 and side arm 35 are each placed into the hemostasis valve 32 that has a front entrance port 37 (as seen in FIGS. 4A and 4B). As seen in FIG. 4B, within the hemostasis valve 32 is a diaphragm 36 through which a guiding catheter or similar catheter can be placed. The purpose of the diaphragm 36 is to prevent the backward flow of blood whether or not any catheter is placed through that diaphragm 36. To decrease the force that is required to either advance a guiding catheter through the hemostasis valve diaphragm 36 in a forward direction or pull a guiding catheter back out of the diaphragm 36, such a diaphragm 36 could be treated with a lubricious, typically hydrophilic, coating such as those used on some introducer sheaths. FIGS. 3, 4A and 4B also show that the adhesive pad 40 includes a spongy pad 41, a tab 42 to remove the adhesive pad 40 from the patient's skin after the procedure is completed and a tab 43 that is used to pull a plastic cover sheet 46 off of the pressure sensitive adhesive 45. The use of a comparatively thick and spongy adhesive pad 41 allows the hemostasis valve 32 to be more effectively joined by the pressure sensitive adhesive 45 to a surface of the skin that could be somewhat irregular. The plastic sheet 46 that covers the pressure sensitive adhesive 45 is removed just before the adhesive pad 40 is attached to the patient's skin. It is also conceived that the spongy pad 41 could be impregnated and elute an antibiotic medication to reduce the probability of infection.

Figure 5:
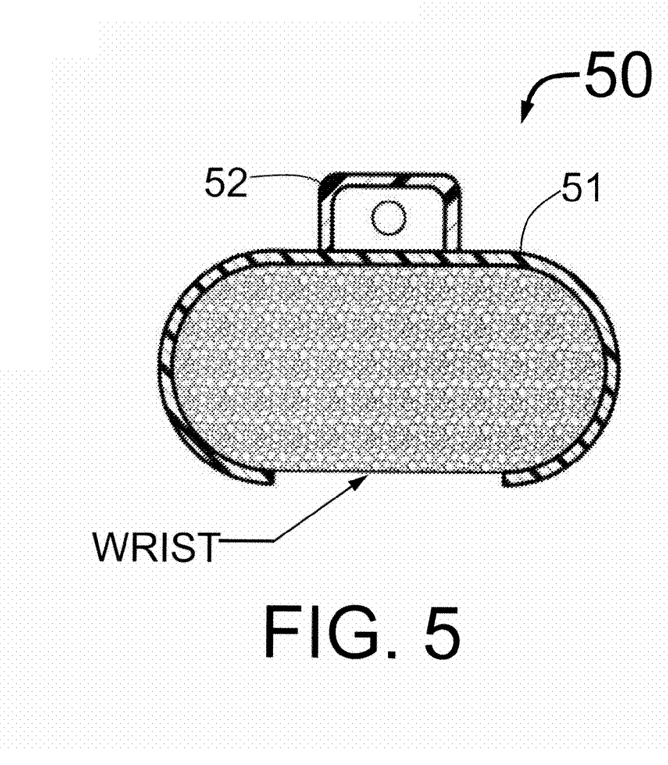
FIG. 5 is across section of the wrist at the site of the hemostasis valve with an adhesive wrap connected to the bottom surface of the hemostasis valve, the adhesive wrap being placed around a patient's wrist.

FIG. 5 is a cross section of an introducer sheath 50 showing a hemostasis valve 52 that has an adhesive pad 51 attached to its bottom surface. The adhesive pad 51 could be partially or completely wrapped around the patient's wrist to secure the introducer sheath 50 to the patient's wrist.

Figure 6:
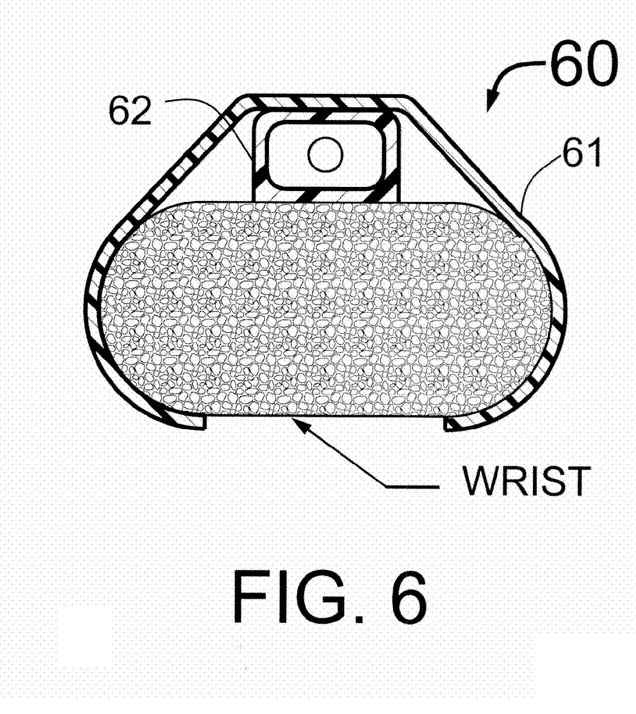
FIG. 6 is a cross section of the wrist at the site of the hemostasis valve with an adhesive wrap connected to the top surface of the hemostasis valve, the adhesive wrap being placed around a patient's wrist.

FIG. 6 is a cross section of an introducer sheath 60 showing a hemostasis valve 62 that has an adhesive pad 61 attached to its top surface. The adhesive pad 61 could be partially or completely wrapped around the patient's wrist to secure the introducer sheath 60 to the patient's wrist.

Figure 7:
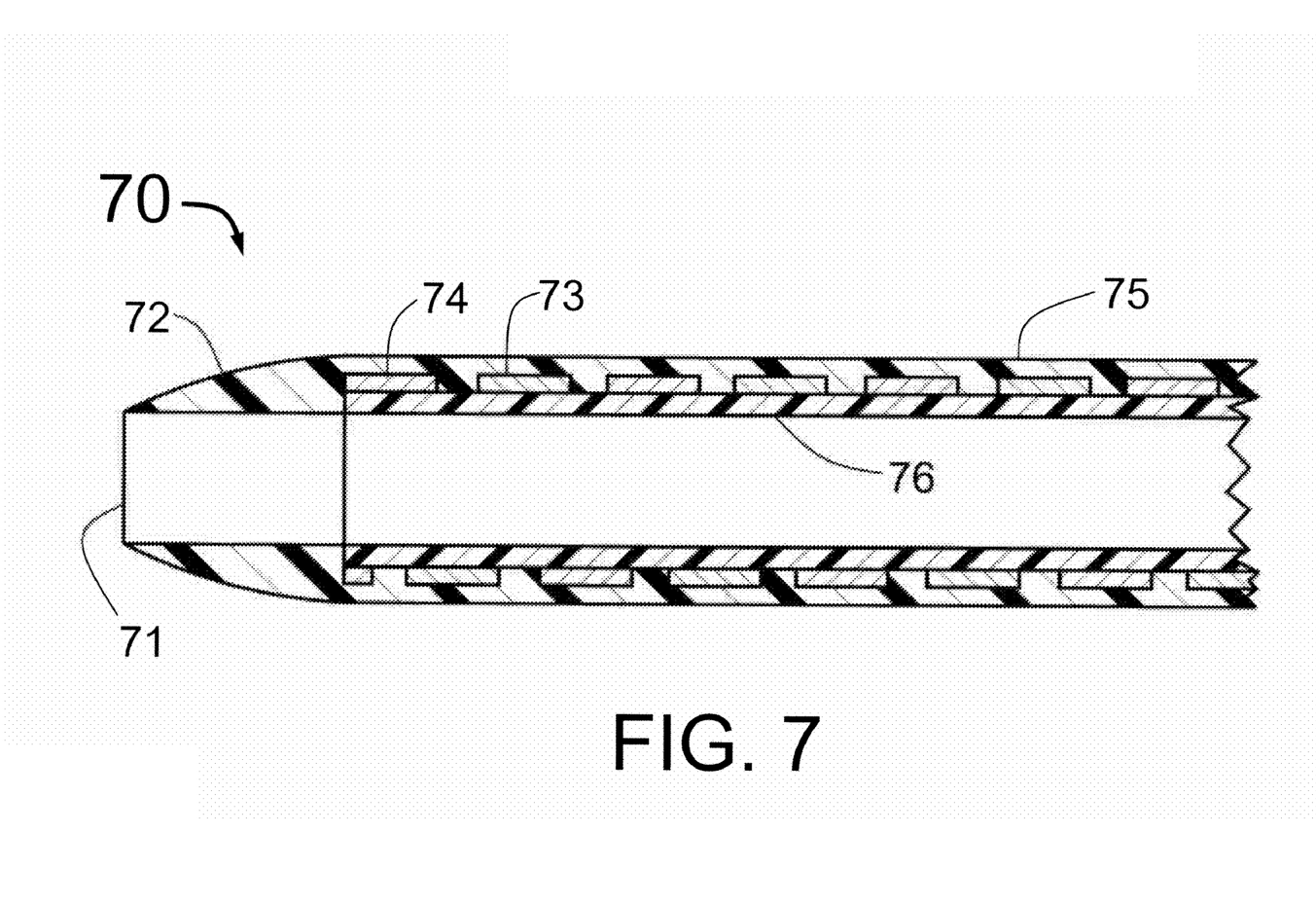
FIG. 7 is a cross section of a distal portion of a thin-walled shaft of an introducer sheath utilizing two helices of different metal alloys each helix having a specific characteristic that is advantageous for the design and functioning of the sheath.

FIG. 7 is another feature of the present invention showing a sheath shaft 70 of a novel, thin-walled design which has a distal opening 71 and a tapered distal end 72. To minimize the opening in the patient's skin, the shaft 70 should be as thin-walled as can be achieved. To have a very thin wall, the shaft 70 could be fabricated from two or more thin-walled metal helical coils 73 and 74 with plastic material on either or both of its interior and exterior surfaces. The inner plastic layer 76 might typically be made from PTFE or any similar Teflon-like, slippery material. The outer plastic layer 75 could typically be Pebax or any similar polymer. The helical metal coils 73 and 74 would be fabricated from flat wires that would optimally be approximately 1 to 3 mils in thickness and about 10 to 30 mils in width. The space between coils would be between 1 and 30 mils with the optimal spacing being between one tenth and nine tenths of the wire's width. The metal for each of the coils 73 and 74 could be stainless steel, a shape memory alloy or a cobalt chromium alloy (such as L605) or any equivalent metal. A key feature of the shaft 70 is that the flat wires 73 and 74 would be made from different metal alloys. Although FIG. 7 shows two helices of flat wire 73 and 74, it should be understood that as many as four separate flat wires could be used for the shaft 70. Optimally at least one of the flat wires would be stainless steel because that is an inexpensive metal alloy. If radiopacity is desired for the shaft, then at least one of the two to four wires would be made from a very dense metal alloy such as the cobalt-chromium alloy L605. If a shape memory alloy is desired to increase resistance against kinking of the sheath, then the metal alloy Nitinol could be used for at least one of the flat wires for the shaft 70. The Nitinol would be treated to maintain its helical shape at a temperature that is below body temperature and preferably below room temperature. The advantage of Nitinol is that in its superelastic state above the transition temperature, such a shaft 70 would be non-kinking even though it would have a very thin wall. An optimum design to achieve radiopacity with minimum cost would be to have one helical coil fabricated from a cobalt-chromium alloy flat wire and one to three additional coils would be made from stainless steel to minimize the coat of the shaft material. An optimum design to avoid kinking of the shaft would use one helix of Nitinol and a second helix of stainless steel to minimize cost of the shaft material.

By having very thin flat wire coils 73 and 74 and a thickness of plastic on each side of that metal coil that is just a few mils thick, the outside diameter of such a shaft 70 would be very much smaller than the outside diameter of any existing introducer sheath having the same inside diameter. An optimum thickness for the shaft 70 would be less than 7 mils and still better, it would be approximately 5 mils in thickness. It is also conceived that a very small diameter wire with a circular cross section could be used instead of the flat wire to form the helical structure to support the tubular shaft of the introducer sheath. Still further, the flat wire could be formed as a braid which is two flat wire helical coils that are interlaced. The present invention conceives that this structure with such an extremely small wall thickness constitutes a significant improvement over the prior art. What the present invention claims is a new concept of thin-walled introducer sheaths whose outside diameter is at least 1.0 French size smaller than any other introducer sheath of comparable inside diameter and optimally a full 1.5 French size smaller outside diameter. Such a reduction in the outside diameter of the introducer sheath's shaft 70 can significantly reduce bleeding at the patient's groin which bleeding can require that the patient requires a blood transfusion. Thus, the present invention claims a method for decreasing the percentage of patients who require a blood transfusion after an introducer sheath has been used to access the patient's vascular system. This method includes forming of a thin-walled, flat-wire, sheath made from two different metal alloys onto which a plastic material is placed onto each side of the helical coil. The method also includes the step of forming the wall thickness of a tubular shaft 70 to be less than 7 mils and as small as 5 mils. The final aspect of this method is to use such a thin-walled tubular shaft as part of an introducer sheath that is used to access a patient's vascular system.

Figure 8:
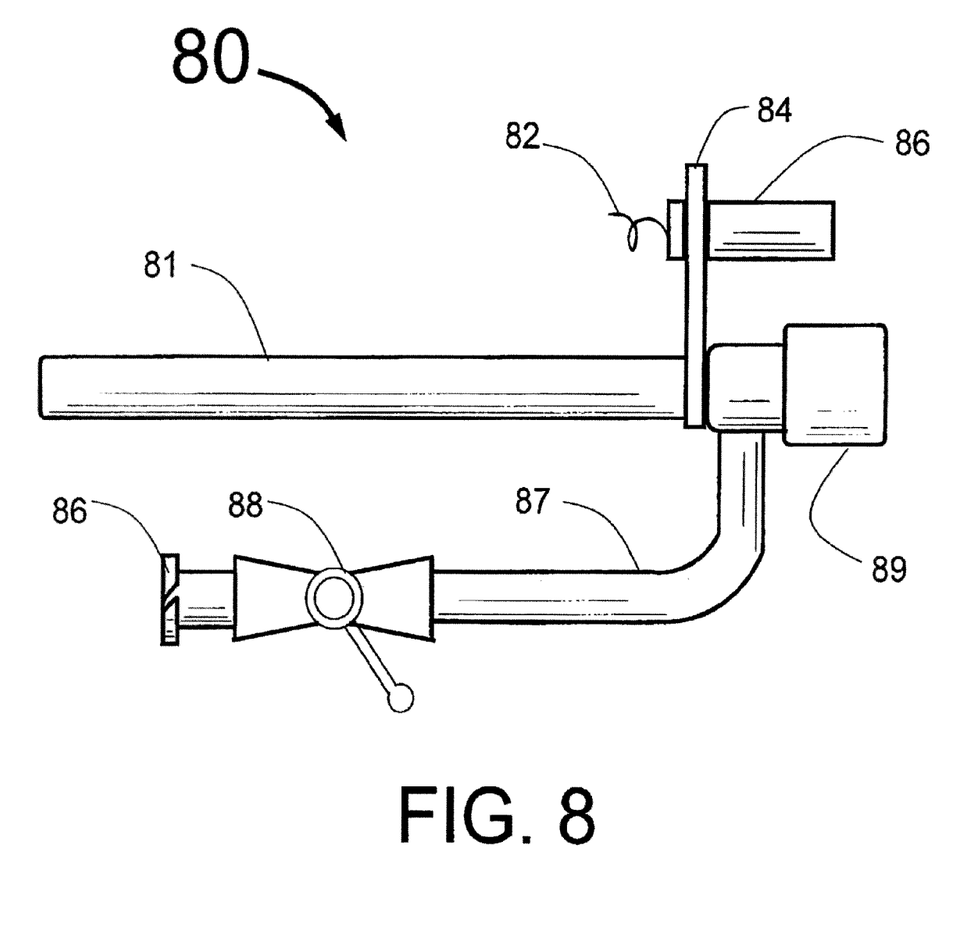
FIG. 8 is a drawing of still another embodiment of the present invention sheath having a corkscrew-like, self-taping wire for affixing the proximal end of the sheath at the insertion site.

FIG. 8 is a sketch of still another embodiment of the present invention sheath 80 having a corkscrew-like, self-taping wire 82 with handle 86 and connector 84 for affixing the proximal end of the sheath 80 to the skin near the insertion site. The sheath 80 also includes hemostasis valve 89, shaft 81, side arm 87 with valve 88 and Luer attachment port 86. By providing the corkscrew wire 82 and handle 86 which is turned like a corkscrew to screw the wire 82 into the patient's skin, it saves time for the doctor who does not need to apply a separate suture to attach the proximal end of the sheath 70 to the patient's skin. It should be noted that the handle 86 and corkscrew 82 could be rotated by 90 degrees from the position shown in FIG. 80 in order to more readily attach the corkscrew 82 to the patient's skin. It is also envisioned that to save time, instead of a corkscrew wire 82 and handle 86, the integrated attachment means could be a needle and suture cord that could be attached to the hemostasis valve so as to not require a separate suture.

Various other modifications, adaptations and alternative designs are of course possible in light of the teachings as presented herein. Therefore it should be understood that, while still remaining within the scope and meaning of the appended claims, this invention could be practiced in a manner other than that which is specifically described herein.

What is claimed is:

1. A method to decrease the need for a patient to require a blood transfusion after an introducer sheath has been used to access that patient's vascular system, the method including the following steps:
   1) obtaining an introducer sheath that has a tubular shaft with an inner lumen sized such that at least one catheter can be inserted therethrough, the tubular shaft comprising an inner plastic layer, a wire layer, and an outer plastic layer, wherein the wire layer is formed from at least two thin-walled, flat wire, helical coils formed from at least two different metal alloys, the at least two thin-walled flat wire helical coils being wound parallel to each other to form a single layer of metal coils for minimizing the wall thickness of the introducer sheath, wherein all the wires in the wire layer are non-overlapping, wherein the tubular shaft comprises a distal portion and a proximal portion, the outer plastic layer of the distal portion having a lubricious coating and the outer plastic layer of the proximal portion being free of a lubricious coating;
   2) placing the thin-walled introducer sheath through the patient's skin and into the patient's vascular system such that part of the proximal portion of the tubular shaft that is free of a lubricious coating is disposed at the vascular entry site in the patient's skin; and
   3) introducing a catheter through the introducer sheath.

2. The method of claim 1 where the metal alloy used for at least one coil is either Nitinol or cobalt-chromium alloy and at least one other helical coil is made from stainless steel.

3. The method of claim 1 where the metal wire thickness is less than or equal to approximately 3 mils and the wall thickness of the tubular shaft is less than approximately 7 mils.

4. The method of claim 1 where the length of the proximal portion being free of a lubricious coating is less than 5.0 cm.

5. A method to decrease the need for a patient to require a blood transfusion after an introducer sheath has been used to access that patient's vascular system, the method including the following steps:
   1) obtaining an introducer sheath that has a tubular shaft with an inner lumen sized such that at least one catheter can be inserted therethrough, the tubular shaft comprising an inner plastic layer, a wire layer, and an outer plastic layer, wherein the wire layer is formed from at least two thin-walled, flat wire, helical coils being wound parallel to each other to form a single layer of metal coils for minimizing the wall thickness of the introducer sheath, where at least one helical coil is made from a cobalt-chromium alloy that is radiopaque and at least one helical coil is made from either stainless steel or Nitinol, wherein all the wires in the wire layer are non-overlapping;
   2) placing the thin-walled introducer sheath through the patient's skin and into the patient's vascular system; and
   3) introducing a catheter through the introducer sheath.

6. The method of claim 5 where the metal wire thickness is less than or equal to approximately 3 mils and the wall thickness of the tubular shaft is less than approximately 7 mils.

7. The method of claim 5 where at least one helical coil is made from stainless steel.

* * * * *